(12) United States Patent
Bayford et al.

(10) Patent No.: US 9,125,583 B2
(45) Date of Patent: Sep. 8, 2015

(54) DETECTION OF CANCER WITH ELECTRICAL IMPEDANCE TOMOGRAPHY

(75) Inventors: Richard Harold Bayford, London (GB); Ivan Maurice Roitt, London (GB); Thomas William Rademacher, Oxford (GB); Andreas Demosthenous, Herts (GB); Raymond Kruse Iles, Welwyn Garden (GB)

(73) Assignees: Middlesex University Higher Education Corporation (GB); Midatech Limited (GB)

( * ) Notice: Subject to any disclaimer, the term of this patent is extended or adjusted under 35 U.S.C. 154(b) by 183 days.

(21) Appl. No.: 13/127,423

(22) PCT Filed: Nov. 6, 2009

(86) PCT No.: PCT/GB2009/051493
§ 371 (c)(1),
(2), (4) Date: May 3, 2011

(87) PCT Pub. No.: WO2010/052503
PCT Pub. Date: May 14, 2010

(65) Prior Publication Data
US 2011/0212029 A1    Sep. 1, 2011

(30) Foreign Application Priority Data
Nov. 6, 2008    (GB) .................................. 0820309.3

(51) Int. Cl.
*G01N 33/574* (2006.01)
*A61B 5/053* (2006.01)
*A61K 49/00* (2006.01)

(52) U.S. Cl.
CPC .............. *A61B 5/0536* (2013.01); *A61K 49/00* (2013.01); *G01N 33/574* (2013.01); *Y10T 428/2982* (2015.01)

(58) Field of Classification Search
CPC ... A61B 5/0033; A61B 5/0536; A61B 5/0537
See application file for complete search history.

(56) References Cited

U.S. PATENT DOCUMENTS

| 4,863,715 A | 9/1989 | Jacobsen |
| 5,688,486 A | 11/1997 | Watson et al. |
| 5,746,214 A * | 5/1998 | Brown et al. ................. 600/547 |
| 5,760,191 A | 6/1998 | Snow et al. |
| 6,207,134 B1 * | 3/2001 | Fahlvik et al. ............. 424/9.322 |
| 6,498,945 B1 | 12/2002 | Alfheim et al. |
| 2005/0079131 A1 * | 4/2005 | Lanza et al. ................. 424/1.11 |
| 2007/0160572 A1 * | 7/2007 | Tamarkin et al. ............ 424/85.1 |
| 2007/0258908 A1 | 11/2007 | Lanza |
| 2008/0243049 A1 | 10/2008 | Hardy |

FOREIGN PATENT DOCUMENTS

WO    WO-2007/122388 A1    11/2007

OTHER PUBLICATIONS

Cheng, K.T. (NCBI Bookshelf, Molecular Imaging and Contrast Agent Database, Bethesda, MD, NCBI Jun. 4, 2008).*
Tzahar and Yarden (Biochimica et Biophysica Acta 1377 (1998) M25-M37).*
Waage et al. (Blood Nov. 1992 : 80:2577-2583),"Waage".*
Fass, L (Molecular Oncology May 10, 2008, 2:115-152).*
Hainfeld et al; J. Histochem. Cytochem.; 48 (4); (2000); 471-480).*
Hainfeld J. F. et al. (Physics in Med. Biol. 2004 49:N309-N315).*
"International Application Serial No. PCT/GB2009/051493, International Search Report mailed Jan. 21, 2010", 4 pgs.
"International Application Serial No. PCT/GB2009/051493, International Preliminary Report on Patentability dated May 10, 2011", 7 pgs.
"International Application Serial No. PCT/GB2009/051493, Written Opinion mailed Jan. 21, 2010", 6 pgs.
Bayford, R. H., "Bioimpedance Tomography (Electrical Impedance Tomography)", *Ann. Rev. Biomed. Eng.*, 8, (2006), 63-91.
Cherepenin, V. A., et al., "Three-Dimensional EIT Imaging of Breast Tissues: System Design and Clinical Testing", *IEEE Transactions of Medical Imaging*, 21(6), (2002), 662-667.
Chester, K., et al., "Engineering Antibodies for Clinical Applications in Cancer", *Tumor Biology*, 25, (2004), 91-98.
De La Fuente, J. M., et al., "Cell Response to Magnetic Glyconanoparticles: Does the Carbohydrate Matter?", *IEEE Transactions on Nanobiosciences*, 6(4), (2007), 275-281.
Oh, T. I., et al., "Multifrequency EIT system with radially symmetric architecture: KHU Mark 1", *Physiology Measurement*, 28, (2007), S183-S196.
Trono, J., et al., "Cellular Uptake of Gold Nanoparticles into Normal and Cancer Cells", *WC 2009, IFMBE Proceedings 25/VIII.* (2009), 202-205.

* cited by examiner

*Primary Examiner* — Peter J Reddig
(74) *Attorney, Agent, or Firm* — Schwegman Lundberg & Woessner, P.A.

(57) ABSTRACT

The use of nanoparticles for imaging a tumor in a mammal using electrical impedance tomography. The nanoparticles comprise a core of metal and/or semiconductor atoms to which are linked ligands that comprise a molecule capable of attaching to a specific tumor biomarker.

7 Claims, 5 Drawing Sheets

DETECTION OF CANCER WITH ELECTRICAL IMPEDANCE TOMOGRAPHY

The present invention relates to a new method for imaging tumours by detecting tumour biomarkers. It may also be used for killing tumour cells. The imaging method may be used to visualise primary lesions in cancers such as colon, prostate, breast and brain cancer, and in the early location of metastases.

Magnetic Resonance Imaging (MRI) and Computer Tomography (CT) ideally provide high resolution body maps of solid tumours, but only if the cancer is sufficiently large. Imaging cancer by Positron Emission Tomography (PET) depends upon metabolic activity rather than size. However, like CT, PET requires the use of ionising radiation with potential oncogenic effects which makes both techniques unsuitable for asymptomatic population screening. In addition, all these technologies are expensive and the instruments used have limited portability.

Electrical Impedance Tomography (EIT) is an imaging technique in which an image of the conductivity or permittivity of a part of a body is inferred from surface electrical measurements. Conducting electrodes are attached to the skin of the subject and small alternating currents applied to some or all of the electrodes. The resulting electrical potentials are measured and the process repeated for numerous different configurations of applied current. The voltages measured are then passed to a computer to perform the reconstruction algorithms and display the resulting image.

There is a range of clinical applications to which EIT has been applied with varying degrees of success. EIT has been used to produce 3-dimensional images of in vivo breast tissue from women with different hormonal status using a circular grid or array of 256 electrodes (see Cherepenin, V. A., IEEE Transactions of Medical Imaging, (2002), 21 (6), 662-667). In a larger study a probe containing a square grid of 64 electrodes was used to examine the breasts of a group consisting of 83 carcinomas and 378 benign cases. The study achieved a sensitivity of 84% and a specificity of 52% suggesting that the false-negative rate may be 10% less than that of traditional mammography which uses ionizing radiation. (see Bayford R. H., *Ann. Rev. Biomed. Eng.*, (2006), 8, 63-91). Whilst existing EIT imaging can provide information on the location of a tumour, it is unable to define its boundaries with any accuracy. Oh, T. I. et al describe a multifrequency EIT System in *Physiol. Meas*, (2007), 28 S183-S196.

There is a need for a low cost technique for imaging tumours in the early stage of their development. In particular, there is a need for an imaging technique that will define the boundaries of the tumour and/or locate metastases. Preferably the equipment should be portable, such that it can be used at the bedside, and use non-ionizing radiation.

It has now been found that by targeting nanoparticles to a tumour and detecting the location of the nanoparticles using electrical impedance tomography, a more accurate image of the tumour can be produced when compared with the previously used non-EIT techniques.

WO 2007/122388 describes nanoparticles for providing immune responses for the treatment or prophylaxis of infection by infectious agents such as viruses, parasites, bacteria, prions and fungi. The nanoparticles comprise a core including metal and/or semiconductor atoms, which core is covalently linked to a plurality of ligands. The ligands include a carbohydrate residue capable of stimulating an innate immune response, or T cell helper peptide and a danger signal. The nanoparticles may incorporate one or more further ligands that are capable of producing a specific response to a target infectious agent.

According to one aspect of the invention there is provided a method of obtaining an image of a tumour located in a body of a mammal such as a human, the method comprising targeting a nanoparticle to the tumour and detecting the location of the nanoparticle using electrical impedance tomography. Preferably multi-frequency electrical impedance tomography (MfEIT) is used.

According to a second aspect of the invention there is provided the use of electrical impedance tomography in combination with nanoparticles for imaging a tumour. The EIT can be used for detecting nanoparticles to which are attached ligands such as antibodies or fragments thereof which are capable of attaching to a biomarker on a tumour.

According to another aspect of the invention there is provided a nanoparticle having attached thereto a ligand such as an antibody or fragment thereof capable of attaching to a tumour biomarker for use in imaging a tumour using electrical impedance tomography.

According to yet another aspect of the invention there is provided the use of nanoparticles for imaging a tumour using electrical impedance tomography.

A biomarker is a biochemical feature that can be used to measure the progress of disease or the effects of treatment. Many cancers abnormally secrete proteins, including growth factors that constitute biomarkers of malignancy. In the case of cancer, a biomarker can indicate the early stage in the development of a tumour. Thus, imaging of tumour biomarkers which include tumour associated antigens, would be very beneficial in the early detection of cancer and/or localisation of metastases.

Nanoparticles are small particles, having a core comprising metal and/or semiconductor atoms, that can be uses as a substrate for immobilizing one or more ligands. The ligands may be covalently linked to the nanoparticles and may be selected from carbohydrates, peptides, therapeutic agents, such as anticancer or cytotoxic drugs, and antibody molecules or fragments thereof, which are capable of targeting a tumour by attaching to a specific tumour biomarker. Examples of specific tumour biomarkers that may be targeted include CEA (carcinoembryonic antigen) on the surface of colon cancer cells, tumour biomarker epidermal growth factor, HER-2 a surface biomarker for breast cancer, EGFR (endothelial growth factor receptor) and cMet (mesenchymal-epithelial transition factor) both biomarkers for brain tumours, PSCA (prostate stem cell antigen) for prostate cancer).

The core material for a metal nanoparticle can be gold, ferrous iron, silver, copper or platinum or combinations thereof, for example an alloy selected from Au/Ag, Au/Cu, Au/Ag/Cu, Au/Pt, Au/Fe, Au/Cu or Au/Fe/Cu.

Preferably the nanoparticles have cores having mean diameters between 0.5 nm and 10 nm, more preferably between 1 nm & 2.5 nm.

The ligands may be conjugated with the core of the nanoparticle by a linker. The linker may comprise a thiol group, and a C2 to C12 alkyl group, or C2 to C12 glycol group or a peptide group. An example of a thiol group linker is represented by the general formula $HO\text{-}(CH_2)_n\text{---}S\text{---}S\text{---}(CH_2)_m\text{---}OH$ wherein n and m are independently between 1 and 5. When the nanoparticles are synthesised, the —S—S— of the linker splits to form two thio linkers that can each covalently attach to the core of the nanoparticle via a —S-group. Ligands such as carbohydrates, peptides, antibody molecules and fragments thereof, and therapeutic agents, such as anticancer or cytotoxic drugs, may all be linked simultaneously or in pre-selected combinations to the core of the nanoparticles.

When the ligands are conjugated to the nanoparticle core with or without a linker, the mean diameter of the nanoparticle including ligands is from 5 nm to 100 nm, preferably from 10 nm to 50 nm, most preferably from 15 nm to 30 nm.

Whereas normal blood vessels (except at an inflammatory site) only permit the egress of 10 nm sized particles from the circulation, the endothelial cells of tumour vasculature allow the passage of 100 nm diameter entities. By coating the nanoparticles with molecules such as antibody fragments bound by different linkers, the nanoparticles can be made of sufficient size to exploit the greater leakiness of the tumour blood vessels, thereby differentially targeting the nanoparticles to the tumour. This selectivity can be augmented by warming with microwaves or alternating magnetic fields focused onto the location of the tumour. These allow deeper interstitial penetration of a tumour mass.

Nanoparticles bearing surface glucose molecules are hydrophilic and form a clear water-like liquid in aqueous media which is well tolerated in vivo. Such nanoparticles may be selectively taken up by metabolically active tumours. Uptake of the nanoparticles is dependent on the size of the particle, the incubation time and the concentration of particles. The nanoparticles can be coated with a ligand comprising an antibody or a small fragment of an antibody specifically recognizing an antigen associated with a particular type of cancer, for example Carcinoembryonic Antigen (CEA) molecules on the surface of colon cancer cells. Such an antibody will attach to the tumour associated antigen and may be taken intracellularly by endocytosis. Even greater selectivity for the tumour cell can be achieved by coating the nanoparticles with two or more different antibody fragments or a bi-specific antibody directed to two distinct tumour-associated antigens. Most tumours can be targeted by nanoparticles bearing glucose or folic acid which bind to glucose or folic acid surface transporters respectively.

In addition to antibody or antibody fragment ligands, the nanparticles may have anticancer drugs, for example doxorubicin and/or cytotoxic compounds attached to them in order to treat the tumour to which they become attached or entrapped within. Alternatively or additionally, a plurality of different types of nanoparticles may be employed together. The mean number of total ligands linked to an individual nanoparticle core is at least one ligand, preferably at least 20 ligands, more preferably at least 50 ligands and most preferably at least 100 ligands.

The intracellular entrapment of the nanoparticles may be achieved by using a non-cleavable linker to attach the 3' end of the anti-sense strand of a small interfering siRNA targeted to the mRNA of a tumour surface antigen so that the intracellular nanoparticles become entrapped in the tumour cell through binding to the cytoplasmic splicer complex. For example, nanoparticles coated with antibody directed to the HER-2 surface biomarker for breast cancer may become trapped within the tumour cell in this way.

Another cancer that may be visualised by targeting nanoparticles to the tumour and then detected by the location of the nanoparticles using EIT is brain cancer. The method according to the invention can be used to detect the brain tumour biomarkers EGFR and cMet. Brain tumours that may be identified include Glioblastoma multiforme, which are the most common primary brain tumours in adults, and malignant astrocytomas. Using targeted nanoparticles, especially gold nanoparticles, and EIT it may also be possible to image malformations in the brain and lesions caused by Alzheimers, stroke or Parkinson's disease.

Once the nanoparticles having ligands such as tumour specific antibodies linked thereto have attached themselves to the tumour surface biomarker or entered the tumour cell by endocytosis, their presence on/in the tumour can be detected using electrical impendance tomography (EIT) preferably MfEIT (multifrequency EIT). MfEIT works by reconstructing the differences in electrical conductivity inside the body caused by an abnormal cellular structure such as a tumour. An arrangement of electrodes is placed on the subject to be imaged and small electrical currents at different frequencies are applied in a well-defined sequence and the voltages that arise from these currents are analysed. The electrode system required for imaging a tumour will vary depending on the tumour. Thus, for example, a 16 electrode system may suffice for imaging colon cancer, whereas for breast and brain imaging 64 to 128 electrodes may be required. The currents used are relatively small, and certainly below the threshold at which they would cause stimulation of nerves. The frequency of the alternating current is sufficiently high not to give rise to electrolytic effects in the body and the Ohmic power dissipated is sufficiently small and diffused over the body to be easily handled by the body's thermoregulatory system.

Utilising the conductivity and permittivity properties of nanoparticles, in particular gold nanoparticles, a greatly enhanced EIT image of a tumour can be obtained. Bioimpedance of a human body produces a great deal of information about the changes of the body during different kinds of activities. For example, the measured impedance is dependent on the amount of water in the body. The measurement of bioimpedance is not just limited to tissue water. It includes the characterization and identification of cells based on their impedance, which differs between cells based on the size, orientation, and membrane thickness, among other factors. This phenomenon may be exploited in EIT, where the impedance information is used to form images of the contents of the human body. In EIT, by injecting a range of currents at several different frequencies, different physiological mechanisms can be identified depending on the chosen frequency range, such as the identification of blood volume changes or cancer cells. By injecting current patterns over a range of frequencies (from 20 Hz to 10 MHz) a spectral image of tissue can be produced. This image represents the three dimensional distribution of the impedance. The use of targeted nanoparticles in accordance with the invention enhances the impedance of affected tumour tissue. Using multifrequency analysis and image reconstruction algorithms the EIT image is greatly enhanced.

Using EIT, especially MfEIT, has the advantage that the imaging technique does not emit potentially ionising radiation like CT or X-Rays and, unlike MRI and CT, is silent, highly portable and inexpensive. In addition the nanoparticles can be a delivery platform for cytotoxic drugs. Alternatively, when the nanoparticles are designed to be trapped within the tumour cells, several methods may be employed to destroy the tumour cells. For example, it may be possible to destroy the tumour cells by focusing external ionizing radiation on them.

Embodiments of the present invention will now be described by way of example and without limitation with reference to the accompanying figures.

The present invention will be further described by way of reference to the following examples.

EXAMPLE 1

Two 140×20 mm petri dishes were prepared each containing a set 1% agarose gel. A solution (20 μl) of gold nanoparticles (obtain from Midatechgroup Ltd) containing the following: 2.26×10E16 particles/ml or 1.147 mg/ml nanoparticles or 37.5 uM nanoparticles was injected into the centre of one of the petri dishes.

16 electrodes were placed around the edge of each petri dish. In order to perform the EIT imaging an adjacent measurement protocol was used in which a 5 mA sinusoidal current was injected at 1 khz using a KUL EIT system (see Physiol. Meas., (2007), 28 S183-S196). The adjacent measurement protocol injects a current on two adjacent electrodes and measures the remaining electrode pairs except for the pairs adjacent the injection electrodes. This is repeated for all the injection pairs until 208 measurements are made.

The set of measurements taken from each of the petri dishes was processed by differencing the data sets and normalising with a reference. This normalised boundary data (The normalised boundary data means two sets of measurements are taken, one without nanopariticles and the second with, then difference the data set and divide by the data set without nanoparticles) was reconstructed with a linear Truncated singular value decomposition algorithm (TSVD). 20 SV's (Singular values) were chosen for the reconstruction. (See Bayford R. H., *Ann. Rev. Biomed. Eng.*, (2006), 8, 63-91).

The reconstructed image was then scaled and displayed with a display programme written in Matlab (Matlab is a mathematical programming tool see (www.mathworks.com)).

Figure 1:
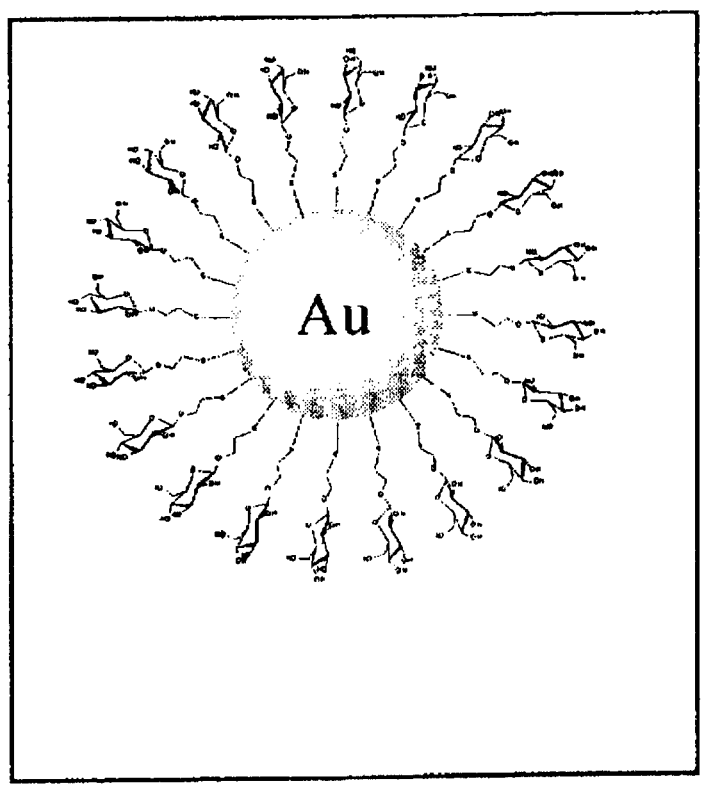
FIG. 1 depicts a gold nanoparticle with sugars attached.
Figure 2:
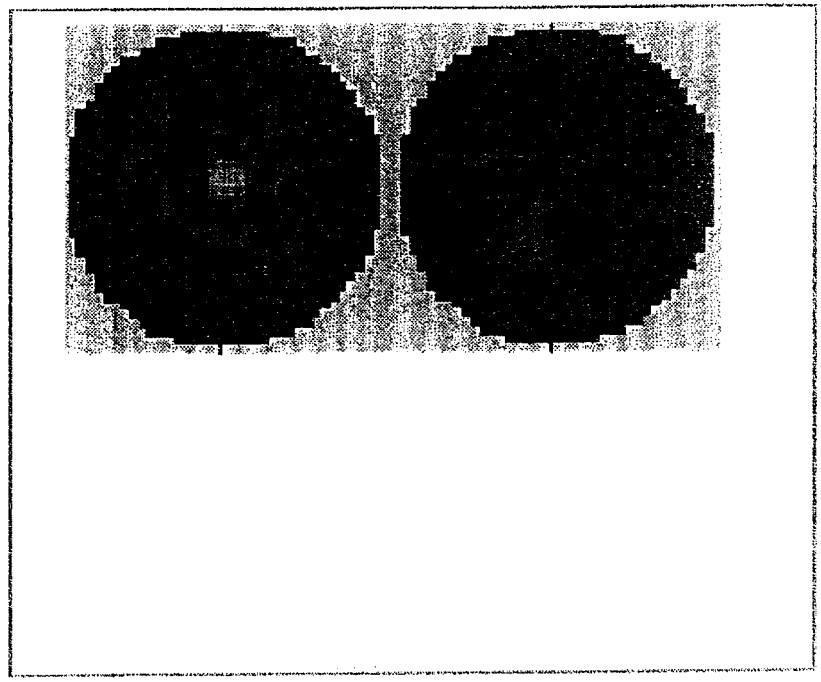
FIG. 2 shows the EIT image of two petri dishes, the left hand dish contained gold nanoparticles, the right hand dish was the control.

The EIT images are shown in FIG. 2 with the left-hand image showing the gold nanoparticles placed in the centre of the agarose gel. The image on the right is the control image produced without the gold nanoparticles being present in the agarose gel.

EXAMPLE 2

Uptake of Glucose-Conjugated Gold Nanoparticles (glc-GNP) in the Colorectal Cancer Cell Line HCT-116

Method

Cells of the colorectal cell line the HCT-116 were maintained in DMEM (Dulbecco's minimal essential medium) supplemented with 10% fetal calf serum containing 25 mM glucose (DMEM-glucose). Unless stated otherwise the DMEM-glucose medium was changed to complete DMEM supplemented with 25 mM D-xylose and 170 nM bovine insulin at −26 hrs (glucose starvation). Four hrs later (−22 hrs) glc-GNP was added. The cells were harvested at 0 hrs, washed three times with phosphate buffered saline (PBS) before they were released from the plastic surface with trypsine. After two additional washings with PBS the cells were lysed with 0.5 ml 1 M NaOH for 24 hrs at room temperature. 4.5 ml PBS was added and the concentration of Au associated with or taken up by the HCT-116 cells was determined with ICP (Inductive coupled plasma)-spectroscopy (Thermo Scientific iCAP 6000 Spectrometer) using TraceCERT Gold Standard for ICP (Sigma) to generate a standard curve.

Results

Figure 3:
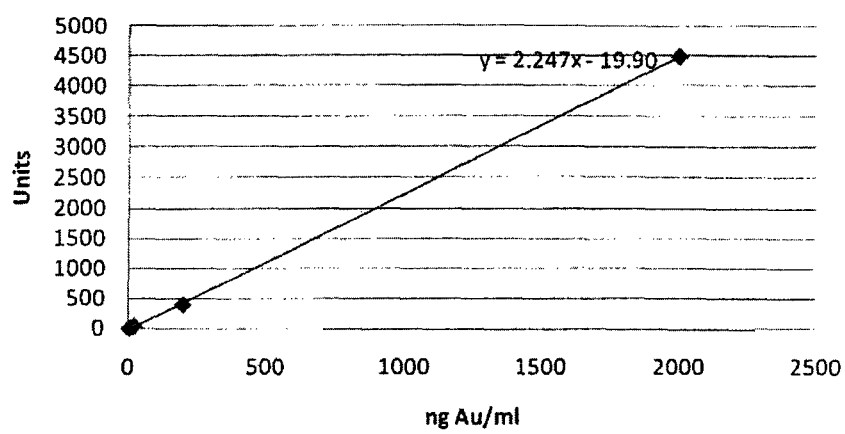
FIG. 3 is an inductive-coupled plasma adsorption emission spectroscopy standard curve.

The ICP-AES (Inductive-coupled plasma adsorption emission spectroscopy) has a linear detection range of gold from 1 ng/ml to >2000 ng/ml as shown in the ICP-AES standard curve of FIG. 3.

Figure 4:
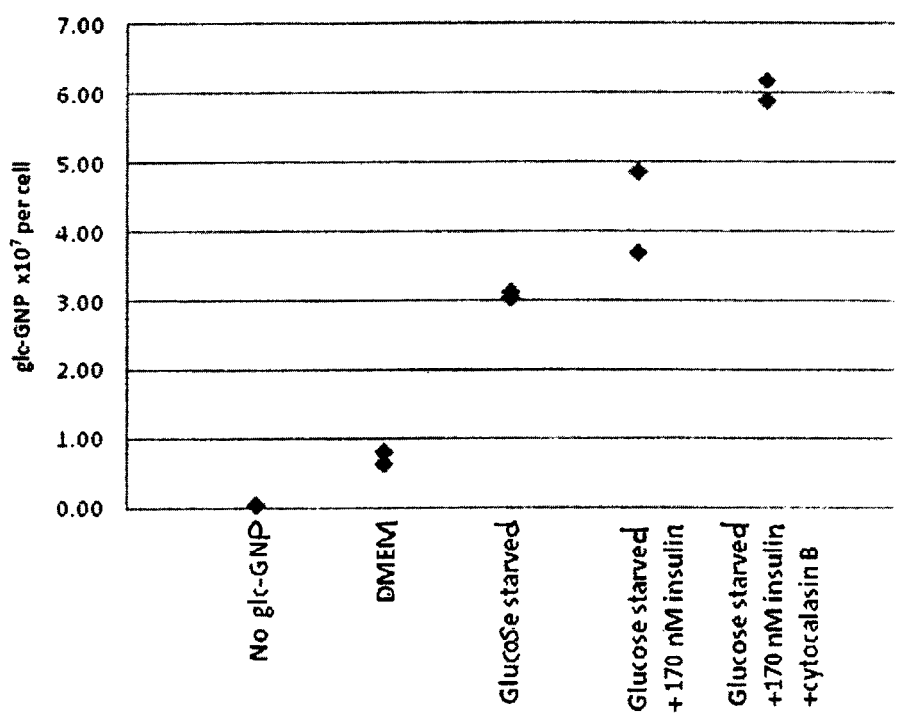
FIG. 4 is a graph showing the uptake of glc-GNP (glucose-gold nanoparticles) when glucose-deprived HCT-116 cells are incubated with glc-GNP.

FIG. 4 shows the effect of glucose starvation for 24 hrs in the absence and presence of 170 nM bovine insulin. 24 hrs glucose starvation enhances the uptake of glc-GNP three fold from ~0.7×10$^7$ glc-GNP taken up per cell to 3.1×10$^7$ glc-GNP per cell in line with the presumed de-regulation of Glut-1 expression with a further increase to 4.3×10$^7$ particles per cell when the cells were subjected to glucose starvation in the presence of 170 nM bovine insulin. This supports the notion that the glucose transporter 1 (glut-1) is implicated in the uptake of the glc-GNP.

Experiment 2 Concentration-Dependent Uptake.

Figure 5:
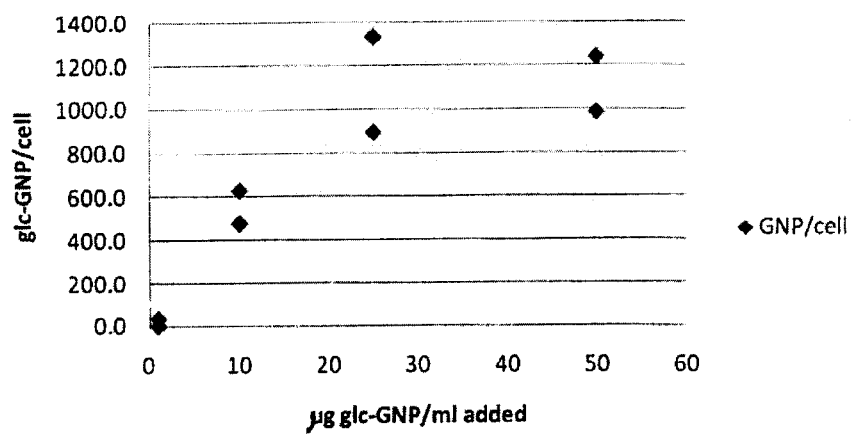
FIG. 5 is a graph showing the uptake of glc-GNP (glucose-gold nanoparticles) when HCT-116 cells are incubated with increasing concentration of glc-GNP.

To investigate the optimal concentration of glc-GNP that the cells can take up, glucose starved and insulin stimulated HCT-116 cells were incubated with increasing concentration of glc-GNP for 22 hrs:

As can be seen from FIG. 5 the experiment shows a linear concentration-dependent uptake reaching a maximum at 25 mμ glc-GNP.

Conclusion

These experiments demonstrate that glc-GNP can be taken up by HCT-116 colorectal cancer cells grown in vitro through a mechanism that appears to involve the glucose transport system 1 (glut-1) although the data suggests that the mechanism is distinct from the way glucose is being internalised.

The invention claimed is:

1. A method of obtaining an image of a tumour located in a body of a mammal, said method comprising targeting nanoparticles to the tumour, said nanoparticles having a metal core of mean diameter of from 0.5 nm to 10 nm and of core material consisting of gold or a combination of gold and ferrous iron, and a ligand linked to the core and capable of attaching to a tumour biomarker and imaging the tumour by detecting location of the nanoparticles attached to the tumour using electrical impedance tomography (EIT).

2. The method of claim 1 wherein the EIT is multi frequency EIT (MfEIT).

3. The method of claim 1 wherein the ligands are selected from the group consisting of carbohydrates, peptides, antibody molecules or fragments thereof.

4. The method of claim 1 wherein the ligand is an antibody molecule or a fragment thereof capable of attaching to a specific tumour biomarker.

5. The method of claim 4 wherein the tumour biomarker is selected from the group consisting of carcinoembryonic antigen (CEA), HER-2, epidermal growth factor (EGF) and mesenchymal-epithelial transition factor (cMet).

6. The method of claim 1 wherein the ligands in addition include therapeutic agents.

7. The method of claim 6 wherein the therapeutic agents are anticancer or cytotoxic drugs.

* * * * *